United States Patent [19]

Ross

[11] 4,275,000
[45] Jun. 23, 1981

[54] PEPTIDE MACROMOLECULAR COMPLEXES

[75] Inventor: Walter C. J. Ross, Sunbury on Thames, England

[73] Assignee: National Research Development Corporation, London, England

[21] Appl. No.: 934,710

[22] Filed: Aug. 21, 1978

[30] Foreign Application Priority Data

Aug. 22, 1977 [GB] United Kingdom ............... 35173/77

[51] Int. Cl.³ .................. A61K 39/385; A61K 39/44; C07G 7/00; C12N 9/96
[52] U.S. Cl. .......................... 260/112 R; 260/112 B; 260/112.5 R; 260/121; 424/85; 424/87; 424/88; 424/92; 424/177; 435/188
[58] Field of Search ............ 260/112 R, 121, 112.5 R, 260/112 B, 112.5; 424/85, 88, 92, 121, 85, 177; 195/63, 68; 435/188

[56] References Cited

U.S. PATENT DOCUMENTS

| | | | |
|---|---|---|---|
| 3,775,253 | 11/1973 | Dieter et al. | 260/112 R X |
| 3,843,447 | 10/1974 | Burkoth | 260/112 R |
| 3,969,287 | 7/1976 | Jaworek et al. | 260/112 R X |
| 4,007,089 | 2/1977 | Smith | 260/112 R X |
| 4,029,766 | 6/1977 | Helting | 260/112 R X |
| 4,066,505 | 1/1978 | Schneider | 260/112 R X |
| 4,081,329 | 3/1978 | Jaworek et al. | 260/112 R X |
| 4,096,138 | 6/1978 | Scherr | 260/121 |
| 4,098,645 | 7/1978 | Hartdegen et al. | 260/112 R |
| 4,101,380 | 7/1978 | Rubinstein et al. | 260/112 R X |
| 4,133,949 | 1/1979 | Batz et al. | 260/121 |
| 4,172,072 | 10/1979 | Ashmead | 424/177 X |

OTHER PUBLICATIONS

Thorpe et al., *Nature*, vol. 271 (Feb. 1978), pp. 752-755.

*Primary Examiner*—Howard E. Schain
*Attorney, Agent, or Firm*—Donald Brown

[57] ABSTRACT

Macromolecular complexes which comprise a first and a second macromolecular moiety joined by a link derived from a linking agent having two or more reactive groups, one of these reactive groups being an activated acyl group, an isocyanate, an isothiocyanate, an iminoether, an iminothioether or an activated halogen atom attached to an aromatic ring and being capable of reacting with one of the macromolecules from which the macromolecular moieties are derived, under conditions where the remaining reactive group, or groups which is or are each an aziridine ring, an aryl azido group or a halogen atom in an α-position relative to a carbonyl group or two carbon atoms removed from a heteroatom carrying a lone pair of electrons, is or are substantially unreactive.

Methods are provided for making the complexes and so are uses for the complexes. Pharmaceutical formulations containing the complex as are provided.

22 Claims, No Drawings

PEPTIDE MACROMOLECULAR COMPLEXES

The present invention relates to macromolecular complexes, a method of making them and pharmaceutical compositions containing them. More specifically the method of making the complexes involves linking two macromolecules through a linking agent having two or more reactive groups of different reactivity.

It is known to bind together macromolecules through an intermediate linking agent having a number of reactive groups and the complexes formed thereby have wide application. For example, enzymes may be linked to water-insoluble carriers and thereby insolubilised; drugs may be linked to carrier proteins (e.g. specific antibodies) to enable them to be localised at the site where the drug is required; or carrier proteins may be linked to liposomes containing entrapped drugs and derived from phospholipids having a reactive end group, again permitting localisation of drugs at specific sites.

A common method of linking macromolecules comprises the reaction, in a single step, of the two macromolecules and the linking agent. In such a reaction dimers or polymers of the macromolecules used are formed as well as the desired adduct. This dimerisation or polymerisation is disadvantageous because:

(i) the yield of the desired product is reduced;

(ii) macromolecules, which are expensive and/or only obtained with difficulty, remain unreacted or become dimerised or polymerised;

(iii) the by-products may be undesirable and difficult to remove.

Also, perhaps more importantly, single step coupling can lead to the formation of intramolecular bonds, thus inhibiting or destroying the biological activity of the macromolecule.

We have now found that these problems may be mitigated or overcome by preparing such complexes in a stepwise manner by first reacting one of the macromolecules with a first reactive site on the linking agent and then reacting the intermediate so formed with the second macromolecule at a second reactive site on the linking agent, as shown in the following sequence:

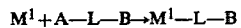  Step 1

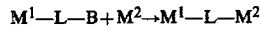  Step 2 in which $M^1$ is a first macromolecule; $M^2$ is a second macromolecule; and A is a first reactive group and B is a second reactive group on a linking group L. Strictly speaking, the group L need not remain unchanged during the steps, because there is no need for the groups A and B to be completely lost; they (or one of them) may become incorporated in a modified form in L. Accordingly the steps may be expressed as:

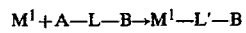  Step 1

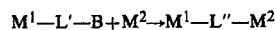  Step 2 in which $M^1$, $M^2$, A, B and L are as defined above and L' may be the same as L or a modified version of L (derived from A and L) and L" may be the same as L' or a modified version of L' (derived from L' and B). For brevity hereinafter the symbol L is used solely but should be considered to include the possibilities of L' and L" as the context requires.

In order that such a stepwise reaction may be effected it is necessary that the conditions under which the first reaction (between $M^1$ and the group A) occurs are such that the second group B will not react with molecule $M^1$. This is important in linking macromolecules of biological origin which contain a multiplicity of functional groups.

Linking agents suitable for use in the present invention include those in which the first group, A, will undergo reaction at a temperature, pH or level of irradiation at which the second group, B, is not reactive.

Reactive groups suitable for use as group A (the more reactive group) in such linking agents include (a) activated carboxyl groups, for example those of formula —COX in which X is a halogen atom, e.g. chlorine or bromine, (to give acid halides); an azido group —N$_3$; the residue of an organic acid, e.g.

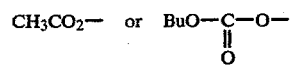

(to give acid anhydrides) or the residue of an alcohol e.g.

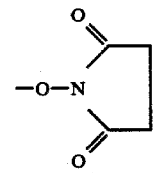

(to give activated esters) which will react with amino functions of macromolecules to give amide links; (b) isocyanate or isothiocyanate groups which react with amino groups, for example, as follows:

(c) iminoethers (or iminothioethers) which react with amino groups, for example, thus (for iminoethers)

(d) compounds bearing activated halogeno groups on aromatic rings, e.g.

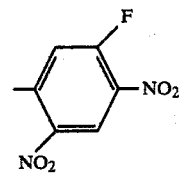

Suitable reactive groups B are activated halogen groups i.e. halogen groups two carbon atoms removed from a heteroatom carrying a lone pair of electrons (electron releasing group) for example halogen groups in radicals such as

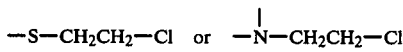

(mustards) (which are unreactive at the lower temperatures at which the aforementioned activated carboxyl groups may be made to react) or halogen atoms in an α-position relative to a carbonyl group e.g. in α-halocarboxylic acids; the heterocyclic aziridine ring-N which is stable at neutral or alkaline pH but which undergoes ring opening at acid pH; and an arylazido group which becomes reactive on irradiation with light.

Linking agents which are preferably used in the method of the invention are:

acyl derivatives of chlorambucil (4-(bis(2-chloroethyl)amino)benzene butanoic acid), e.g.

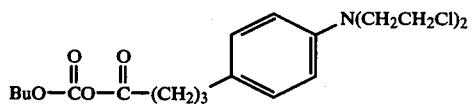

and of 4-(2-chloroethyl)amino benzene butanoic acid, e.g.

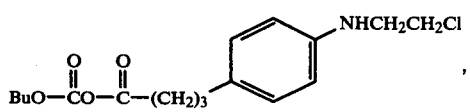

the acyl groups of which will undergo reaction with primary or secondary amino groups at less than 10° C., preferably less than 5° C., and the chloroethyl amino groups of which will react with amino or carboxyl groups at 25° to 30° C. At a pH of about 9 the chloroethylamino groups react preferentially with amino groups in the macromolecule $M^2$ and as the pH is lowered the amount of such reaction with amino groups decreases, i.e. the reaction with carboxyl groups becomes relatively more important. A further way of increasing the difference in reactivities between the A and B groups, when the B group is a halogen group two carbon atoms removed from a heteroatom carrying a lone pair of electrons, is to carry out the A-group reaction in the presence of a high concentration, e.g. greater than 1 molar, of halide, e.g. chloride, ions as this reduces further the reactivity of the B group. When the B-group is reacted later, the reaction should preferably be carried out in the presence of a lower concentration of the halide ions, the halide ion concentration being reduced between steps, e.g. by ultrafiltration. This halide ion concentration adjustment is particularly suitable for the present class of linking agents.

Other linking agents that may be used include acyl derivatives of 2,4-dinitro-5-aziridinyl-benzoic acid, for example the mixed anhydride:

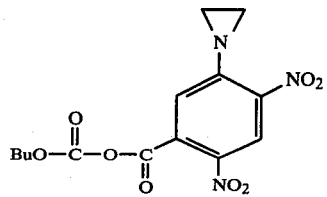

in which the acid anhydride group will react at alkaline or neutral pH with primary or secondary amino groups on the macromolecule $M^1$ to give amide links, with the aziridine ring being opened at acid pH by carboxyl groups on the macromolecule $M^2$; and acyl derivatives of 5-azido-2,4-dinitrobenzoic acid, e.g.

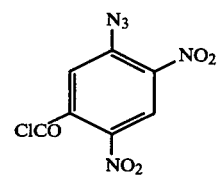

in which the acid chloride group reacts with amino group under conditions of low radiation intensity, e.g. in a dark room, the azide group then reacting, after elimination of a molecule of nitrogen, by insertion into a C—H bond when irradiated with visible light of a suitable higher intensity.

The linking group L of the linking agent serves as a carrier for the two reactive groups A and B and may be any group which serves such a purpose, provided that the differential activity between the groups A and B (as herein defined) is retained. The linking agent portion L may advantageously contribute to the differential reactivity of groups A and B. The group L used will generally be dictated by the availability or ease of synthesis of the linking agent A—L—B and conveniently the two groups A and B are attached to an aromatic ring or rings, preferably a benzene ring.

It is essential that the linking agent contains only one of the more reactive groups A in order to prevent dimer or polymer formation in the first step of the reaction. It is further preferable that only one group B is present in the linking agent, although the use of linking agents having two or more of such groups is not precluded.

In conducting the stepwise reaction hereinbefore described it is preferred to isolate and purify (for example by chromatography) the product of the first step before the second linking reaction is performed, to remove unreacted linking agent and, if desired, any unreacted macromolecule or any by-product, the presence of which is undesirable. It will in general also be necessary to purify the final product to remove any unreacted starting materials or undesirable side product.

It is also to be understood that, in common with macromolecular chemistry in general, the products obtained by the method of the invention will not consist of a single chemical entity but will comprise a series of conjugates falling within a molecular weight band, by which they may be characterised. The degree of variation will depend upon the number and variety of functional groups in the macromolecules $M^1$ and $M^2$.

It is normally preferred that the products obtained by the method of the present invention have a ratio of 1:1 with respect to the two macromolecules $M^1$ and $M^2$. In order that such a ratio may be obtained it is desirable, in the reaction between $M^1$ and A—L—B, that the intermediate complex obtained is of the form $M^1$—$(L—B)_n$, where n is greater than 1, and thus the intermediate complex itself will not be a single chemical entity but a series of complexes comprising macromolecules having a varying number of linking groups attached thereto. It is advisable to produce intermediate complexes of this type as in the second step not all of the groups B in the linking molecules will react with the second macromolecule $M^2$ because of side reactions, for example with the solvent or with other components in the reaction mixture.

Control over the ratio of $M^1$ to $M^2$ is further complicated by the fact that in the second step two or more of the intermediate complexes represented by $M^1$—L—B may react together, rather than with $M^2$, to give further intermediates of the type represented by $M^1$—L—$M^1$—L—B which may themselves react with either $M^2$ or a further molecule $M^1$—L—B.

In both steps reaction techniques known in the art for controlling undesirable side reactions, e.g. using an excess of one component or by adding a component to the reaction mixture continuously during the course of the reaction, may be employed to try to obtain the desired ratio.

Any macromolecules containing suitable functional groups may be linked by using linking agents containing the aforementioned groups, although the method is particularly applicable to macromolecules of biological origin, such as peptides e.g. proteins, especially antigens, antibodies, enzymes, lipoproteins, serum albumins, toxins and toxoids. In peptides, the macromolecule $M^1$ usually reacts via its amino groups and macromolecule $M^2$ reacts for example via its amino or carboxyl groups, or C-H bonds.

The method of the present invention is particularly useful for linking together a chemotherapeutic agent, e.g. diphtheria toxin, to an antibody, i.e. immunoglobulin, since the complex so produced is thereby rendered site specific and the chemotherapeutic agent may be concentrated at the required point, thereby reducing the dose required and hence side-effects whilst at the same time improving the therapeutic effect of the therapeutic agent.

The complexes of the present invention, especially the biologically active ones, may be used for a variety of purposes. For example, anti-cancer agents of improved selectivity for treatment of the disease in a mammal, including man, may be obtained by linking a tumour-specific antibody to the original anti-cancer agent. Improved immunosuppressive agents for treatment or prophylaxis in a mammal, including man of for example, graft versus host (GVH) disease or transplant (graft) rejection by a host mammal and autoimmune diseases may be obtained, for example, by linking one or more toxins to an anti-lymphocytic globulin. Further, anti-parasitic agents for treatment or prophylaxis of diseases in a mammal, including man, caused by parasites may be obtained by linking an antibody for the parasite e.g. Trypanosoma cruzi, to a toxin, e.g. diphtheria toxin. These complexes may be used in the treatment of the diseases referred to.

Complexes of the present invention may be used as reagents in enzyme linked immunosorbent assay (E.L.I.S.A.) reactions. For this use an antibody to the substance being detected is labelled by being linked to an enzyme suitable for catalysing a readily monitored reaction. The complexes obtained by the present process generally have greater activity than complexes produced by earlier methods.

The amount of therapeutic complexes required for therapeutic effect will of course vary with the particular complex used and the disease being treated. In general a suitable dose for a mammal of a complex of the invention will lie in the range of $10^{-6}$ to 10 molar equivalents of the amount of the particular chemotherapeutic agent in the complex which would be required in its unbound form for the therapeutic effect obtained.

The carrier used in a pharmaceutical formulation may be any that is acceptable, i.e. does not have any substantially deleterious effect on the recipient. The carrier used for a particular administration will depend upon the route used, which would usually be parenteral; for example a liquid, e.g. aqueous, carrier would be suitable for parenteral administration, e.g. intravenous injection. A suitable aqueous carrier is water for injections.

The formulations of the present invention in liquid media may be freeze-dried for convenient storage.

It will be appreciated from the foregoing that what we claim may comprise any novel feature described herein, principally and not exclusively:

(a) a method of linking macromolecules comprising the steps of:

(i) reacting a first macromolecule $M^1$ with a linking agent A-L-B wherein A is a first reactive group selected from an activated acyl group (as herein defined), an isocyanate or isothiocyanate, an iminoether, an iminothioether or an activated halogen atom attached to an aromatic ring and B represents one or more second reactive groups selected from an activated halogeno group (as herein defined for B groups), an aziridine ring or an aryl azido group under reaction conditions where the group A is reactive but B is not reactive to give an intermediate $M^1$—L—B;

(ii) optionally, isolating and purifying the so-produced intermediate;

(iii) reacting the intermediate $M^1$—L—B with a second macromolecule $M^2$ under reaction conditions where the group B is reactive to give a complex $M^1$—L—$M^2$; and (iv) isolating the so-produced complex;

(b) a macromolecular complex which comprises a first and a second macromolecular moiety joined by a link derived from a linking agent having two or more reactive groups, one of these reactive groups being an activated acyl group, an isocyanate, an isothiocyanate, an iminoether, an iminothioether or an activated halogen atom attached to an aromatic ring and being capable of reacting with one of the macromolecules from which the macromolecular moieties are derived, under conditions where the remaining reactive group, or groups which is or are each an aziridine ring, an aryl azido group or a halogen atom in an α-position relative to a carbonyl group or two carbon atoms removed from a heteroatom carrying a lone pair of electrons, is or are substantially unreactive;

(c) a pharmaceutical composition comprising a biologically active macromolecular complex according to the invention together with an acceptable carrier therefor.

The following Examples illustrate the invention.

EXAMPLE 1

The coupling of anti-lymphocytic globulin to diphtheria toxin using chlorambucil residue as a linking group Solution (A): 61 mg butyl chloroformate made up to 5.4 ml in dry dioxan.

Solution (B): 0.115 ml triethylamine made up to 10 ml in dry tetrahydrofuran.

Chlorambucil (25 mg) was dissolved in solution (B) (1.0 ml) and to an aliquot (0.3 ml) of the solution obtained was added solution (A) (0.3 ml). The reaction mixture was then stirred in an ice bath for 30 minutes.

The reaction mixture was added to a solution of horse anti-human lymphocytic globulin (ALG; 50 mg) in a mixture of saline borate (SB) buffer (0.05 M borate buffer containing 1.7% sodium chloride, fungicidal and bacteriostatic agents, pH 8.9-9.1) (5 ml) and dioxan (1.4 ml) and stirred at 4° C. for 90 minutes to form a conjugate.

This solution was applied (at 4° C.) to a jacketed Sephadex SG 25 column (Pharmacia) and eluted with SB buffer at a flow rate of 40 ml/hour.

The protein band (detected on an LBK flow-through Spectrophotometric cell at 281 nm) (20 ml) was collected and concentrated to 2.5 ml in an Amicon ultrafiltration cell. A sample (0.1 ml) of the concentrate was diluted for spectrophotometric estimation of the level of binding of chlorambucil to the ALG (all done in a cold room at 4° C.).

The concentrated conjugate solution (1 ml) was added to diphtheria toxin (1.05 ml) (25 mg/ml+0.05 ml of $I^{125}$-radio-labelled toxin) and stirred at room temperature for 30 hours.

A precipitate formed; the suspension was centrifuged (at 2,000 G), and the supernatant applied to a Sephadex SG 150 S/F column (K16/90) (Pharmacia) and eluted with SB buffer. Fractions were collected and estimated spectrophotometrically. Samples (0.1 ml) of the fractions were also estimated by dissolving in scintillation fluid and counting.

The high molecular weight fraction having M.wt. of 180,000 to 250,000 comprised a series of conjugates of ALG and diphtheria toxin conjugated through chlorambucil, there being an average of from 1.0 to 1.5 moles of diphtheria toxin conjugated, through a chlorambucil residue, to each mole of ALG. A second high molecular weight fraction (M. wt>250,000) was also obtained.

(i) Integrity of the antigen-binding capacity of the conjugate

This was tested by indirect immunofluorescence. Human lymphoid cell-line cells ($CLA_4$ cells) were incubated (30 minutes, 37° C.) with ALG or the conjugate, ALG-chlorambucil-diphtheria toxin, before washing and incubating with fluorescent rabbit and anti-horse antibodies. The cells were then washed three times and mounted on slides and examined under the fluorescence microscope. The resulting fluorescence is a measure of the amount of ALG or conjugate that bound to the cells during the first incubation so that the minimum concentration of antibody needed to produce visible fluorescence can be determined. The fluorescent titre for ALG-chlorambucil-diphtheria toxin (M.wt 180,000 to 250,000) 1:1 was $3.0 \times 10^{-5}$ mM which is insignificantly different from the titre for ALG alone ($2.6 \times 10^{-5}$ mM). Thus the linkage of diphtheria toxin to ALG did not affect the antigen binding capacity of the antibody. However, the conjugate of M.wt>250,000 did show a somewhat reduced binding capacity, with a titre of $6.6 \times 10^{-5}$ mM.

(ii) The cytotoxic properties of conjugated diphtheria toxin

This was tested using guinea-pig macrophages which non-specifically bind and uptake foreign proteins. The macrophages were contacted for four days with toxin or conjugates; cell survival at the end of this period was determined from the ability of adhering cells to pinocytose neutral red dye which was subsequently extracted and the optical density measured at 540 nm.

ALG-chlorambucil-diphtheria toxin (M.wt 180,000 to 250,000) was as toxic to the macrophages as was diphtheria toxin alone, killing down to $10^{-12}$ M, or about 50 molecules per cell. Thus the coupling of diphtheria toxin to ALG using chlorambucil does not inactivate the toxic properties of the toxin. The conjugate of higher M.wt. (>250,000) did however show a twenty-fold reduction in its capacity to kill macrophages compared to diphtheria toxin.

The specific cytotoxic action of ALG-chlorambucil-diphtheria toxin on human lymphoid cells Having established that we could link ALG to diphtheria toxin in such a manner that neither antigen-binding capacity of the antibody nor toxic properties of the toxin were overly affected by conjugation, the conjugates were tested against their target cell, $CLA_4$, in vitro.

$CLA_4$ cells ($2 \times 10^5$ cells per 200 l culture) in Hanks balanced salt solution containing 10% foetal calf serum were exposed to diphtheria toxin for 1 hour before washing five times. Cell survival was measured at the end of the 24 hours incubation by the ability of the cells to incorporate $^3H$-leucine into protein.

It was found that diphtheria toxin was not very effective at killing $CLA_4$ cells compared with other sensitive cells such as guinea pig macrophages and human fibroblasts. On prolonged (24 hours) exposure diphtheria toxin would only kill $CLA_4$ cells at concentrations down to $10^{-9}$ M, and on short exposure no cell death was apparent even at the maximum concentration used of $10^{-8}$ M. However, the ALG-chlorambucil-diphtheria toxin conjugate (M.W. 180,000 to 250,000) was very potent and killed $CLA_4$ cells at concentrations down to $10^{-11}$ M for both 1 hour and 24-hour exposures. Thus by linking diphtheria toxin to ALG its cytotoxic effect on 1 hour exposure to $CLA_4$ cells was improved by a factor of about 1000. ALG alone did not kill $CLA_4$ cells, and did not modify the toxicity of diphtheria toxin when presented simultaneously to the cells.

Furthermore, when diphtheria toxin was coupled to a non-immune immunoglobulin which had no ability to bind to $CLA_4$ cells, the conjugate was 50 fold less toxic than diphtheria toxin alone so that the improved toxicity of ALG-chlorambucil-diphtheria toxin seems to be specific for the target cell. This is supported by the finding that ALG-chlorambucil-diphtheria toxin was about twenty-fold less efficient at killing human fibroblasts, a cell to which ALG does not bind, than was diphtheria toxin alone.

EXAMPLE 2

The coupling of human γ globulin (HγG) to bovine serum albumin (BSA) using the sodium salt of 2,4-dinitro-5-aziridinyl-benzoic acid as a precursor for the linking agent Solution (A): 0.16 g butyl chloroformate made up to 2.35 ml in dry tetrahydrofuran
Solution (B): 0.15 ml triethylamine made up to 2.50 ml in DMSO.

The sodium salt of 2,4-dinitro-5-aziridinyl benzoic acid (20 mg) was dissolved at room temperature in solution B (0.2 ml) and cooled in ice until just solid when solution A (0.2 ml) was added. The mixture was stirred at room temperature until just fluid and then in an ice-water bath for 20 minutes.

A solution of $I^{125}$-radiolabelled bovine serum albumin (BSA) (50 mg in 1.5 ml SB buffer) was then added rapidly while stirring, and the reaction mixture was left at room temperature for 90 minutes during which time the pH was monitored and N/10 NaOH solution added to keep the pH at 8.0.

At the end of the 90 minutes the whole reaction mixture was applied to a K16/40 Sephadex SG 25 (Pharmacia) column and eluted with SB buffer at a flow rate of 40 ml/hour.

The protein band (detected as described in Example 1) (in 13 ml of eluant) was collected and a sample was diluted for spectrophotometric determination of the level of binding of 2-4-dinitro-5-aziridinyl benzoic acid to the BSA.

The protein band (conjugate) was concentrated to 2.0 ml in an Amicon ultrafiltration cell and the concentrate so obtained was added to HγG (50 mg) in SB buffer (2 ml). The pH at this point was 9.1.

The reaction mixture was stirred rapidly while the pH was adjusted to 5.3 by slow addition of 1 N hydrochloric acid from a microsyringe. When the addition of hydrochloric acid was complete the reaction mixture was stirred in a water bath at 40° C. and the reaction followed spectrophotometrically, small samples being taken every 5 hours, diluted and examined by UV spectroscopy. After 20 hours a shift of λmax from 336 nm to 356 nm indicated that the reaction was complete and the pH was adjusted to 9.1 by slow addition, to the rapidly stirred mixture, of 1 N sodium hydroxide.

A precipitate formed; the suspension was centrifuged and a portion of the supernatant (2.0 ml) was applied to a K16/90 Saphadex SG 150 S/F column (Pharmacia) and eluted with SB buffer.

Fractions from the column were collected, samples (0.1 ml) of the fractions were taken, dissolved in scintillation fluid and counted.

The high molecular weight fraction (M.wt > 150,000) comprised a series of conjugates of bovine serum albumin and human (HγG) having an average of 9 moles of 2,4-dinitro-5-aziridinyl benzoic acid bound to each mole of BSA and to which conjugates was bound 80% of the labelled BSA. It was estimated that the conjugate band contained 1 to 2 molecules of BSA for each molecule of HγG.

EXAMPLE 3

The coupling of proteins to liposomes

Solution (A): 0.1 ml butyl chloroformate made up to 2.16 ml in dry tetrahydrofuran
Solution (B): 0.1 ml triethylamine made up to 2.0 ml in dry DMSO The sodium salt of 2,4-dinitro-5-aziridinyl benzoic acid (30 mg) was added to solution (B) (0.3 ml) and stirred at 0° C. until just solid when solution (A) (0.3 ml) was added and stirred in a jacketed vessel at below 4° C. for 20 minutes. An aliquot (0.4 ml) of the thus obtained reaction mixture was added to a phospholipid (dipalmitoyl phosphatidyl ethanolamine) (30 mg) in washed and dried chloroform (4 ml). The temperature was raised to 50° C. and the reaction was followed by a thin layer chromatography (TLC) on aluminium backed silica gel TLC plates using:
(1) $CHCl_3$:MeOH 20:5, or
(2) $CHCl_3$:MeOH:$H_2O$ 70:30:5

After 2 hours no unreacted phospholipid was detectable in these systems. The reaction mixture was allowed to cool and applied to a dry silica gel column which was washed with chloroform (200 ml) to elute 2 minor bands. The solvent was then changed to chloroform:methanol:water (70:30:5), and the product first being adsorbed on to the top of the column and then eluted as two major bands; when the second band started to elute the solvent was changed to pure ethanol and all the material was eluted from the column.

The conjugate band (the first major band eluted) was dried by evaporation under reduced pressure at less than 40° C., redissolved in chloroform (20 ml), filtered through a Millipore filter (0.22 μm pore size) to remove silica fines and dried by rotary evaporation (reduced pressure and ambient temperature). A yellow liquid residue (presumed to be largely water) remained and was removed by successive addition and evaporation under reduced pressure of dry benzene.

The product travels as a single spot (Rf. 0.6) in the above mentioned TLC systems.

Liposomes are prepared from egg lecithin (10 mg) and dipalmitoyl phosphatidyl ethanolamine (2 mg) (obtained as described above) by the following method. The lipids are mixed and dried as a thin film under reduced pressure on a rotary evaporator at ambient temperature and then suspended in sodium chloride (1 ml, 73 ml) and phosphate buffer (1 mM; pH 7.0); (at this pH the aziridine ring of the 2,4-dinitro-5-aziridinyl benzoic acid residue is poorly reactive).

A solution (2 ml; 15 mg/ml) of bovine serum albumin (BSA) in sodium chloride (73 mM) and acetate buffer (5 mM) is then added and the pH of the mixture is adjusted to 4.1 with aqueous hydrochloric acid. At this pH BSA binds electrostatically to the liposomes (the liposomes are negatively charged, the BSA is net positively charged), and the 2,4-dinitro-5-aziridinyl benzoic acid residue reacts with suitable residues on the liposome. After an 8 hour incubation the pH is adjusted to 7.0 with aqueous sodium hydroxide and the liposomes are separated from unbound BSA by gel chromatography on Sepharose 6B.

EXAMPLES 4–13

General method for coupling protein-1 to protein-2 using chlorambucil residue as linking group Solution (A): 0.1 ml butyl chloroformate made up to 9.5 ml with dry dioxan
Solution (B): 0.1 ml triethylamine made up to 8.7 ml with dry tetrahydrofuran Chlorambucil (7.5 mg) was dissolved in 0.3 ml solution (B) and to the stirred, cooled (2° C.) solution was added 0.3 ml solution (A). After 30 minutes a precooled solution of protein-1 (5 ml 10 mg protein-1 per ml in borate:NaCl (0.05 M:1.7%, pH 9) and dioxan (1.4 ml) was added quickly and stirring continued at 2° C. for 1½ to 2 hours. The solution was then passed through a jacketed (2° C.) column of Sephadex SG 25 and eluted with the same borate-saline buffer.

The protein containing eluate (20 ml)—detected with an LKB flow-through spectrophotometric cell at 280 nm—was run into a solution of protein-2 (1 ml 25 mg protein-2 per ml in the same boratesaline buffer). A small quantity of radio-iodine labelled ($I^{125}$) protein-2 was present to assist quantitation of the results.

The combined solutions were concentrated in an Amicon ultra-filtration cell down to 2 ml and then allowed to stand at 26° C. for 24 hours. After centrifugation to remove any insoluble material the supernatant was passed down a column of Sephadex SG 200 superfine and eluted with the borate-saline buffer of pH 9.

Fractions were collected and the molecular weights were calculated from the elution volumes. The protein-2 content of the fractions was estimated from the gamma-radiation counts and the protein-1 content from the U.V. absorbance at 280 nm after deducting the contribution from protein-2.

Besides fractions containing unconjugated protein-1 and protein-2, fractions of M.wt 180,000 to 250,000 and >250,000 were obtained. The fraction of M.wt 180,000 to 250,000 consisted of conjugates of protein-1 and protein-2, there being an average of 1 to 1.5 molecules of protein-2 coupled to each molecule of protein-1.

For protein-1 it is possible to use normal horse and normal bovine immunoglobulin, horse antimouse thymocytic globulin, horse anti-human lymphocytic globulin and F(ab)₂ fragments (obtained by pepsin digestion) of normal horse immunoglobulin and of horse anti-human lymphocytic globulin. For protein-2 it is possible to use bovine serum albumin, diphtheria toxin and abrin.

When F(ab)₂ fragments are used as protein-1 it is preferable to use Sephadex SG 150 superfine for the final chromatographic separation and in this case the fraction of M.wt 130,000 to 200,000 contained predominantly a 1:1 protein-1:protein-2 conjugate.

The specific couplings set out in Table 1 have been carried out.

TABLE 1

| Example | Protein-1 | Protein-2 |
|---|---|---|
| 4 | normal horse immunoglolin | bovine serum albumin |
| 5 | normal horse immunoglolin | diptheria toxin |
| 6 | normal bovine immunoglobulin | bovine serum albumin |
| 7 | normal bovine immunoglobulin | diptheria toxin |
| 8 | horse anti-mouse thymocytic globulin | " |
| 9 | horse anti-human lymphocytic globulin | bovine serum albumin |
| 10 | horse anti-human lymphocytic globulin | abrin |
| 11 | horse anti-human lymphocytic globulin | diptheria toxin |
| 12 | F(ab)₂ fragments of normal horse immunoglobulin | " |
| 13 | F(ab)₂ fragments of horse anti-human | " |

TABLE 1-continued

| Example | Protein-1 | Protein-2 |
|---|---|---|
| | lymphocytic globulin | |

EXAMPLES 14–26

A portion of each of the complexes formed in Examples 1 to 13 is dispersed into separate aliquots of water for injections so as to form respective solutions suitable for injection.

I claim:

1. A macromolecular complex which comprises a first and a second peptide macromolecular moiety, joined by a link derived from a linking agent having two or more reactive groups, one of these reactive groups being selected from the group consisting of activated acyl groups, isocyanates, isothiocyanates, iminoethers, iminothioethers and activated halogen atoms attached to aromatic rings and being capable of reacting with one of the macromolecules from which the macromolecular moieties are derived, under conditions where the remaining reactive group or groups which is or are each selected from the group consisting of aziridine rings, aryl azido groups and halogen atoms in an α-position relative to a carbonyl group or two carbon atoms removed from a hetero-atom carrying a lone pair of electrons, is or are substantially unreactive.

2. A complex according to claim 1 in which the first and second macromolecules are each selected from the group consisting of antigens, antibodies, enzymes, lipoproteins, serum albumins, toxins and toxoids.

3. A complex according to claim 2 in which either (a) one of the macromolecules is a diphtheria toxin and the other is an antibody or (b) one of the macromolecules is an antilymphocytic globulin and the other is a toxin.

4. A macromolecular complex comprising a first and a second peptide macromolecular moiety, joined by a link derived from a linking agent having two or more reactive groups, in which the link is a radical derived from a compound selected from the group consisting of acyl derivatives of chlorambucil, of 4-(2-chloroethyl)amino benzene butanoic acid, of 2,4-dinitro-5-aziridinylbenzoic acid, and of 5-azido-2,4-dinitrobenzoic acid.

5. A method of linking peptide macromolecules which comprises:

(a) reacting a first peptide macromolecule $M^1$ with a linking agent A—L—B in which A is a first reactive group which is selected from the group consisting of activated acyl groups, isocyanates, isothiocyanates, iminoethers, iminothioethers, activated halogen atoms attached to aromatic rings, L is a linking group joining A and B, and B is a second reactive group or further reactive groups which is or are each selected from the group consisting of aziridine rings, aryl azido groups and halogen atoms in an α-position relative to a carbonyl group or two carbon atoms from a hetero atom carrying a lone pair of electrons, under reaction conditions where the group A is reactive but B is (are) not reactive to give an intermediate $M^1$—L'—B in which L' is the same as L or is derived from L and A (b) reacting the intermediate $M^1$—L'—B with a second peptide macromolecule $M^2$ under reaction conditions where the group B is (are) reactive to give a complex $M^1-L''-M^2$ in which $L''$ is the same as $L'$ or is derived from $L'$ and B; and (c) isolating the complex produced.

6. A method according to claim 5 in which the activated acyl group is selected from the group consisting of acyl halides, acyl anhydrides, acylazides and activated esters.

7. A method according to claim 6 in which the acyl halide, acyl anhydride, acylazide or activated ester is selected from the group consisting of such derivatives of chlorambucil, of 4-(2-chloroethyl)aminobenzene butanoic acid, of 2,4-dinitro-5-aziridinylbenzoic acid, and of 5-azido-2,4-dinitrobenzoic acid.

8. A method according to claim 7 in which the acyl group of the acyl derivative of a compound selected from the group consisting of chlorambucil and 4-(2-chloroethyl)aminobenzene butanoic acid reacts with an amino group in macromolecule $M^1$ at less than 10° C. and the chloroethyl group reacts with a carboxyl or amino group in macromolecule $M^2$ at 25° to 30° C.

9. A method according to claim 7 in which the acyl group of the acyl derivative of a compound selected from the group consisting of chlorambucil and of 4-(2-chloroethyl)aminobenzene butanoic acid reacts, in the presence of a relatively high concentration of halide ions, with an amino group in macromolecule $M^1$ and the chloroethyl group reacts, in the presence of a relatively lower concentration of halide ions, with a carboxyl or amino group in macromolecule $M^2$.

10. A method according to claim 7 in which the acyl derivative of 2,4-dinitro-5-aziridinylbenzoic acid reacts with an amino group in macromolecule $M^1$ at alkaline or neutral pH and the aziridine ring reacts with a carboxyl group in macromolecule $M^2$ at acidic pH.

11. A method according to claim 5 in which the first and second macromolecules are each selected from the group consisting of antigens, antibodies, enzymes, lipoproteins, serum albumins, toxins and toxoids.

12. A method according to claim 11 in which either (a) one of the macromolecules is a diphtheria toxin and the other is an antibody or (b) one of the macromolecules is an anti-lymphocytic globulin and the other is a toxin.

13. A method according to claim 5 in which the linking agent molecule contains only one B group.

14. A method according to claim 5 in which the intermediate $M^1-L'-B$ is isolated and purified before step (b).

15. A macromolecular complex which comprises a first antibody macromolecular moiety and a second enzyme macromolecular moiety joined by a link derived from a linking agent having two or more reactive groups, one of these reactive groups being selected from the group consisting of activated acyl groups, isocyanates, isothiocyanates, iminoethers, iminothioethers and activated halogen atoms attached to aromatic rings and being capable of reacting with one of the macromolecules from which the macromolecular moieties are derived, under conditions where the remaining reactive group or groups which is or are each selected from the groups consisting of aziridine rings, aryl azido groups and halogen atoms in an α-position relative to a carbonyl group or two carbon atoms removed from a heteroatom carrying a lone pair of electrons, is or are substantially unreactive.

16. A method according to claim 5 in which one of the macromolecules is an antibody and the other is an enzyme.

17. A method according to claim 5 in which, following step (a), the reaction conditions are adjusted in temperature or pH so as to cause group B to react under the new conditions with macromolecule $M^2$, although group B had not reacted with macromolecule $M^1$ under the previous conditions.

18. A method according to claim 5 wherein group B is selected from the group consisting of aziridine rings and halogen atoms that are two carbon atoms from a heteroatom carrying a lone pair of electrons.

19. A method according to claim 5 wherein group B comprises

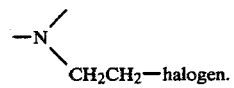

20. A macromolecular complex according to claim 1 wherein group B is selected from the group consisting of aziridine rings and halogen atoms that are two carbon atoms from a heteroatom carrying a lone pair of electrons.

21. A macromolecular complex according to claim 1 wherein Group B comprises

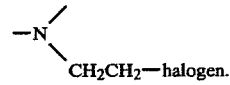

22. A macromolecular complex which comprises a peptide macromolecular moiety and a phospholipid macromolecular moiety joined by a link derived from a linking agent having two or more reactive groups, one of these reactive groups being selected from the group consisting of activated acyl groups, isocyanates, isothiocyanates, iminoethers, iminothioethers and activated halogen atoms attached to aromatic rings and being capable of reacting with one of the macromolecules from which the macromolecular moieties are derived, under conditions where the remaining reactive group or groups which is or are each selected from the group consisting of aziridine rings, aryl azido groups and halogen atoms in an α-position relative to a carbonyl group or two carbon atoms removed from a heteroatom carrying a lone pair of electrons is or are substantially unreactive.

* * * * *